(12) United States Patent
Logan et al.

(10) Patent No.: US 7,066,733 B2
(45) Date of Patent: Jun. 27, 2006

(54) APPARATUS AND METHOD FOR CURING MATERIALS WITH LIGHT RADIATION

(75) Inventors: Joseph N. Logan, Trumbull, CT (US); Raymond L. Knox, Bethel, CT (US)

(73) Assignee: Kerr Corporation, Orange, CA (US)

( * ) Notice: Subject to any disclaimer, the term of this patent is extended or adjusted under 35 U.S.C. 154(b) by 0 days.

(21) Appl. No.: 10/655,781

(22) Filed: Sep. 5, 2003

(65) Prior Publication Data

US 2005/0003322 A1    Jan. 6, 2005

Related U.S. Application Data

(63) Continuation of application No. 09/632,260, filed on Aug. 4, 2000, now Pat. No. 6,692,251, which is a continuation-in-part of application No. 09/009,205, filed on Jan. 20, 1998, now Pat. No. 6,200,134.

(51) Int. Cl.
*A61C 1/00* (2006.01)
*A61C 3/00* (2006.01)

(52) U.S. Cl. .......................................... 433/29; 362/119

(58) Field of Classification Search .................. 433/29, 433/215; 606/1, 13, 16; 607/88; 362/119, 362/800, 804
See application file for complete search history.

(56) References Cited

U.S. PATENT DOCUMENTS

| | | |
|---|---|---|
| 3,638,013 A | 1/1972 | Keller ...................... 240/41.15 |
| 3,712,984 A | 1/1973 | Lienhard |
| 3,733,481 A | 5/1973 | Kuyt |
| 3,868,513 A | 2/1975 | Gonser ........................ 250/504 |
| 3,970,856 A | 7/1976 | Mahaffey et al. ........... 250/493 |
| 4,048,490 A | 9/1977 | Troue ....................... 240/41.35 |
| 4,114,274 A | 9/1978 | Jones |
| 4,114,946 A | 9/1978 | Hoffmeister et al. |
| 4,149,086 A | 4/1979 | Nath |
| 4,184,196 A | 1/1980 | Moret et al. ................... 433/29 |
| 4,185,891 A | 1/1980 | Kaestner ..................... 350/167 |

(Continued)

FOREIGN PATENT DOCUMENTS

DE     42 11 233     1/1992

(Continued)

OTHER PUBLICATIONS

Burgess, John O. et al., *An Evaluation of Four Light-Curing Units Comparing Soft and Hard Curing*, Pract. Periodont Aesthet. Dent. 11(1), 125-132, 1999.

(Continued)

*Primary Examiner*—Ralph A. Lewis
(74) *Attorney, Agent, or Firm*—Wood, Herron & Evans, L.L.P.

(57) ABSTRACT

An instrument and method for curing light-curable compounds in the mouth of a patient, the instrument comprising a housing and a plurality of solid state, light-emitting elements on a substrate supported by the housing. The elements form a collective array on the substrate operable for collectively emitting light having wavelengths within a narrow band of wavelengths.

An optical focusing device is positioned to intercept the light emitted by the array of elements and includes a non-imaging optical device which is operable for collimating the light from the array into a beam to be directed onto a compound for curing the compound. A disposable sleeve covers the housing and array and may incorporate the optical focusing device. The sleeve is removed and discarded after use to eliminate the need to autoclave the instrument.

18 Claims, 3 Drawing Sheets

U.S. PATENT DOCUMENTS

| | | | |
|---|---|---|---|
| 4,186,748 A | 2/1980 | Schlager | 128/736 |
| 4,209,907 A | 7/1980 | Tsukada et al. | |
| 4,229,658 A | 10/1980 | Gonser | |
| 4,230,453 A | 10/1980 | Reimers | 433/29 |
| 4,233,649 A | 11/1980 | Scheer et al. | |
| 4,280,273 A | 7/1981 | Vincent | |
| 4,298,806 A | 11/1981 | Herold | 250/504 |
| 4,337,759 A | 7/1982 | Popovich et al. | 126/438 |
| 4,385,344 A | 5/1983 | Gonser | 362/32 |
| 4,391,588 A | 7/1983 | Matsui | |
| 4,398,885 A | 8/1983 | Loge et al. | 433/126 |
| 4,412,134 A | 10/1983 | Herold et al. | |
| 4,445,858 A | 5/1984 | Johnson | |
| 4,450,139 A | 5/1984 | Bussiere et al. | 422/186.3 |
| 4,610,630 A | 9/1986 | Betush | |
| 4,666,406 A | 5/1987 | Kanca, III | 433/229 |
| 4,673,353 A | 6/1987 | Nevin | |
| 4,716,296 A | 12/1987 | Bussiere et al. | |
| 4,729,076 A | 3/1988 | Masami et al. | 362/235 |
| 4,757,381 A | 7/1988 | Cooper et al. | |
| 4,792,692 A | 12/1988 | Herold et al. | |
| 4,810,194 A | 3/1989 | Snedden | 433/91 |
| 4,826,431 A | 5/1989 | Fujimura et al. | 433/29 |
| 4,836,782 A | 6/1989 | Gonser | |
| 4,839,566 A | 6/1989 | Herold et al. | |
| 4,846,546 A | 7/1989 | Cuda | 350/96.24 |
| 4,888,489 A | 12/1989 | Bryan | 250/504 |
| 4,935,665 A | 6/1990 | Murata | 313/500 |
| 4,936,808 A | 6/1990 | Lee | 445/24 |
| 4,948,215 A | 8/1990 | Friedman | |
| 4,963,798 A | 10/1990 | McDermott | 315/312 |
| 4,999,310 A | 3/1991 | Kim | 437/51 |
| 5,003,434 A | 3/1991 | Gonser et al. | 362/32 |
| 5,007,837 A | 4/1991 | Werly | |
| 5,017,140 A | 5/1991 | Ascher | |
| 5,029,957 A | 7/1991 | Hood | 350/96.2 |
| 5,115,761 A | 5/1992 | Hood | 118/641 |
| 5,147,204 A | 9/1992 | Patten et al. | 433/229 |
| 5,150,016 A | 9/1992 | Sawase et al. | 315/294 |
| 5,161,879 A | 11/1992 | McDermott | 362/206 |
| 5,162,696 A | 11/1992 | Goodrich | 313/511 |
| 5,173,810 A | 12/1992 | Yamakawa | |
| 5,198,678 A | 3/1993 | Oppawsky | |
| 5,201,655 A | 4/1993 | Friedman | 433/29 |
| 5,233,283 A | 8/1993 | Kennedy | 320/13 |
| 5,242,602 A | 9/1993 | Richardson et al. | 210/745 |
| 5,265,792 A | 11/1993 | Harrah et al. | 228/6.2 |
| 5,278,629 A | 1/1994 | Schlager et al. | 356/313 |
| 5,283,425 A | 2/1994 | Imamura | 250/208.1 |
| 5,290,169 A | 3/1994 | Friedman et al. | 433/29 |
| 5,302,124 A | 4/1994 | Lansing et al. | |
| 5,312,249 A | 5/1994 | Kennedy | |
| 5,316,473 A | 5/1994 | Hare | 433/29 |
| 5,328,368 A | 7/1994 | Lansing et al. | |
| 5,371,826 A | 12/1994 | Friedman | 385/115 |
| 5,373,114 A | 12/1994 | Kondo et al. | 174/268 |
| 5,420,768 A | 5/1995 | Kennedy | 362/119 |
| 5,457,611 A | 10/1995 | Verderber | |
| 5,471,129 A | 11/1995 | Mann | 320/21 |
| 5,487,662 A | 1/1996 | Kipke et al. | 433/37 |
| 5,521,392 A | 5/1996 | Kennedy et al. | 250/492.1 |
| 5,530,632 A | 6/1996 | Shikano et al. | |
| 5,535,230 A | 7/1996 | Abe | 372/43 |
| 5,616,141 A | 4/1997 | Cipolla | |
| 5,617,492 A | 4/1997 | Beach et al. | 385/33 |
| 5,634,711 A | 6/1997 | Kennedy et al. | 362/119 |
| 5,660,461 A | 8/1997 | Ignatius et al. | 362/241 |
| 5,664,042 A | 9/1997 | Kennedy | 385/136 |
| 5,698,866 A | 12/1997 | Doiron et al. | 257/99 |
| 5,707,139 A | 1/1998 | Haitz | 362/231 |
| 5,711,665 A | 1/1998 | Adam et al. | 433/9 |
| 5,747,363 A | 5/1998 | Wei et al. | 438/5 |
| 5,759,032 A | 6/1998 | Bartel | |
| 5,803,729 A | 9/1998 | Tsimerman | |
| 5,857,767 A | 1/1999 | Hochstein | |
| 5,912,470 A | 6/1999 | Eibofner et al. | |
| 5,928,220 A | 7/1999 | Shimoji | |
| 5,975,895 A | 11/1999 | Sullivan | |
| 6,008,264 A | 12/1999 | Ostler et al. | 522/4 |
| 6,033,223 A | 3/2000 | Narusawa et al. | |
| 6,045,240 A | 4/2000 | Hochstein | |
| 6,046,460 A | 4/2000 | Mertins | |
| 6,065,965 A | 5/2000 | Rechmann | |
| 6,068,474 A | 5/2000 | Senn et al. | |
| 6,077,073 A | 6/2000 | Jacob | |
| 6,086,367 A | 7/2000 | Levy | |
| 6,095,812 A | 8/2000 | Senn et al. | |
| 6,102,696 A | 8/2000 | Osterwalder et al. | |
| 6,123,545 A | 9/2000 | Eggler et al. | |
| 6,155,823 A | 12/2000 | Nagel | |
| 6,159,005 A | 12/2000 | Herold et al. | |
| 6,161,937 A | 12/2000 | Rosenstatter | |
| 6,168,431 B1 | 1/2001 | Narusawa et al. | |
| 6,171,105 B1 | 1/2001 | Sarmadi | |
| 6,186,786 B1 | 2/2001 | Trushkowsky | |
| 6,193,510 B1 | 2/2001 | Tsimerman | |
| 6,200,134 B1 | 3/2001 | Kovac et al. | 433/29 |
| 6,208,788 B1 | 3/2001 | Nosov | |
| 6,220,722 B1 | 4/2001 | Begemann | |
| 6,280,187 B1 | 8/2001 | Slone | |
| 6,280,188 B1 | 8/2001 | Ross | |
| 6,331,111 B1 | 12/2001 | Cao | |
| 6,345,982 B1 | 2/2002 | Meyer | |
| 6,379,149 B1 | 4/2002 | Franetzki | |
| 6,419,483 B1 | 7/2002 | Adam et al. | |
| 6,439,888 B1 | 8/2002 | Boutoussov et al. | |
| 6,468,077 B1 | 10/2002 | Melikechi et al. | |
| 6,692,251 B1 * | 2/2004 | Logan et al. | 433/29 |
| 2001/0007739 A1 | 7/2001 | Eibofner et al. | |
| 2001/0046652 A1 | 11/2001 | Ostler et al. | |
| 2002/0014864 A1 | 2/2002 | Gemunder et al. | |
| 2002/0051367 A1 | 5/2002 | Hooker et al. | |
| 2002/0133970 A1 | 9/2002 | Gordon et al. | |
| 2003/0015667 A1 | 1/2003 | MacDougald et al. | |
| 2003/0036031 A1 | 2/2003 | Lieb et al. | |
| 2003/0219693 A1 | 11/2003 | Cao | |

FOREIGN PATENT DOCUMENTS

| | | |
|---|---|---|
| DE | 295 11 927 | 2/1997 |
| EP | 0 116 405 | 8/1984 |
| EP | 0 266 038 | 10/1991 |
| EP | 0 568 666 | 11/1992 |
| EP | 0 320 080 | 8/1993 |
| EP | 0 672 435 | 9/1995 |
| EP | 0 678 282 | 10/1995 |
| EP | 0 709 698 | 5/1996 |
| EP | 0 755 662 | 7/1996 |
| EP | 0 736 307 | 10/1996 |
| EP | 0 780 101 | 6/1997 |
| EP | 0 780 103 | 6/1997 |
| EP | 0 830 850 | 3/1998 |
| EP | 0 879 582 | 11/1998 |
| EP | 0 880 945 | 12/1998 |
| EP | 0 884 025 | 12/1998 |
| EP | 0 885 025 | 12/1998 |
| EP | 0 998 880 | 5/2000 |
| EP | 1 031 326 | 8/2000 |
| EP | 1 090 607 | 4/2001 |
| EP | 1 090 608 | 4/2001 |
| EP | 1 093 765 | 4/2001 |
| EP | 1 103 232 | 5/2001 |
| EP | 1 112 721 | 7/2001 |
| EP | 1 138 276 | 10/2001 |

| | | |
|---|---|---|
| EP | 1 138 349 | 10/2001 |
| EP | 0 830 851 | 5/2002 |
| EP | 0 830 852 | 5/2002 |
| EP | 1 206 923 | 5/2002 |
| EP | 1 228 738 | 8/2002 |
| EP | 0 740 567 | 11/2002 |
| GB | 2 212 010 | 7/1989 |
| GB | 2 329 756 | 3/1999 |
| JP | 6-30275 | 9/1995 |
| JP | 8-141001 | 6/1996 |
| JP | 9-10238 | 1/1997 |
| JP | 9010238 * | 1/1997 |
| JP | 8-194786 | 2/1997 |
| JP | 410033573 | 2/1998 |
| JP | 2 080 522 | 11/1999 |
| WO | WO 83/01311 | 4/1983 |
| WO | WO 84/04463 | 11/1984 |
| WO | WO 92/02275 | 2/1992 |
| WO | WO 93/09847 | 5/1993 |
| WO | WO 93/21842 | 11/1993 |
| WO | WO 95/07731 | 3/1995 |
| WO | WO95/19810 | 7/1995 |
| WO | WO 95/26217 | 10/1995 |
| WO | WO/97/36552 | 10/1997 |
| WO | WO 97/37722 | 10/1997 |
| WO | WO 97/46279 | 12/1997 |
| WO | WO 97/46280 | 12/1997 |
| WO | WO 98/03131 | 1/1998 |
| WO | WO 98/04317 | 2/1998 |
| WO | WO 99/09071 | 2/1999 |
| WO | WO 99/11324 | 3/1999 |
| WO | WO 99/16136 | 4/1999 |
| WO | WO 99/20346 | 4/1999 |
| WO | WO 99/35995 | 7/1999 |
| WO | WO 00/01464 | 1/2000 |
| WO | WO 00/02491 | 1/2000 |
| WO | WO 00/13608 | 3/2000 |
| WO | WO 00/15296 | 3/2000 |
| WO | WO 00/41726 | 7/2000 |
| WO | WO 00/41767 | 7/2000 |
| WO | WO 00/41768 | 7/2000 |
| WO | WO 00/43067 | 7/2000 |
| WO | WO 00/43068 | 7/2000 |
| WO | WO 00/43069 | 7/2000 |
| WO | WO 00/45733 | 8/2000 |
| WO | WO 00/67048 | 11/2000 |
| WO | WO 00/67660 | 11/2000 |
| WO | WO 01/03770 | 1/2001 |
| WO | WO 00/14012 | 3/2001 |
| WO | WO 01/19280 | 3/2001 |
| WO | WO 01/24724 | 4/2001 |
| WO | WO 01/54770 | 8/2001 |
| WO | WO 01/60280 | 8/2001 |
| WO | WO 01/64129 | 9/2001 |
| WO | WO 01/68035 | 9/2001 |
| WO | WO 01/69691 | 9/2001 |
| WO | WO 02/06723 | 1/2002 |
| WO | WO 02/09610 | 2/2002 |
| WO | WO 02/11640 | 2/2002 |
| WO | WO 02/32505 | 4/2002 |
| WO | WO 02/33312 | 4/2002 |
| WO | WO 02/49721 | 6/2002 |
| WO | WO 02/056787 | 7/2002 |
| WO | WO 02/069839 | 9/2002 |
| WO | WO 02/080808 | 10/2002 |

OTHER PUBLICATIONS

Davidson-Kaban, Saliha S. et al., *The Effect of Curing Light Variations on Bulk Curing and Wall-to-Wall Quality of Two Types and Various Shades of Resin Composites*. Dent. Mater. 13: 344-352, Nov. 1997.

*European Search Report*, Feb. 27, 2004.

Feltzer, A. J. et al., *Influence of Light Intensity on Polymerization Shrinkage and Integrity of Restoration-Cavity Interface*, Eur. J. Oral Sciences, 103: 322-326, 1995.

Kanca, III, John and Suh, Byoung I., *Pulse Activation: Reducing Resin-Based Composite Contraction Stresses at the Enamel Cavosurface Margins*, Am. J. of Dentistry, 12(3), 107-112, 1999.

Kato, Hiromasa, *Relationship Between the Velocity of Polymerization and Adaptation to Dentin Cavity Wall of Light-Cured Composite*, Dental Materials J. 6(1): 32-37, 1987.

Koran, Peter and Kurschner, Ralf, *Effect of Sequential versus Continuous Irradiation of a Light-Cured Resin Composite on Shsrinkage, Viscosity, Adhesion, and Degree of Polymerization*, Am. J. of Dentistry, 11, No. 1, 17-22, 1998.

LumiLeds Lighting LLC, *Concept Evaluation Data Luxeon™ Star 5-Watt*, Luxeon™ 5-Watt Prelminary Target Data Sheet, Publication No. JP10 (Jan. 2002).

LumiLeds Lighting LLC, *LED Application Note Dental Light Curing*, LumiLeds Lighting Publication No. XXX(03.01), Copyright© 2000.

LumiLeds Lighting LLC, *Application Bulletin AB XXX*, Luxeon™ Data Sheet, Publication No. xxxx-xxxx.

LumiLeds Lighting LLC, *Luxeon™ Power Light Sources of the Future*, Jan. 2001—Mike Holt.

LumiLeds Lighting LLC,*Lumen Maintenance of White Luxeon™ Power Light Sources*, Application Brief AB07, LumiLeds Lighting, US LLC.

LumiLeds Lighting LLC, *Application Note 1149-5, Secondary Optics Design Considerations for Super Flux LEDs*, Copyright© 2000 LumiLeds Lighting, Obsoletes Publication No. 5968-1215E, Publication No. AN06 (Mar. 2000).

Luxeon Dental Technical Data, *Power Light Source*, Apr. 2002.

Mayes, Joe H., *Curing Lights: An Overview*, Unknown, p. 15-17.

Mehl, A. et al., *Physical Properties and Gap Formation of Light-Cured Composites With and Without 'Softstart-Polymerization'*, J. of Dentistry, 25, 321-330, 1997.

Sakaguchi, Ronald L. and Berge, Hong Xu, *Reduced Light Energy Density Decreases Post-Gel Contraction While Maintaining Degree of Conversion in Composites*, J. of Dentistry, 26, 695-700, 1998.

Schlager, Kenneth J., Ignatius, Ronald W., *An LED-Array Light Source for Medical Therapy*, SPIE vol. 1892 Medical Lasers and Systems II (1993) p. 26-35.

Swift Jr., Edward J. et al., Ed., *Contemporary Photocuring Issues, Part II*, J. Esthetic Dentistry, 12 (1), 50-57, 2000.

Tarle, Z. et al., *The Effect of the Photopolymerization Method on the Quality of Composite Resin Samples*, J. of Oral Rehab. 25: 436-442, 1998.

TIR Technologies, Inc., *Miniaturized TIR lenses for Light Emitting Diodes*, TIR Technical Publication, pp. 1-14.

Uno, Shigeru and Asmussen, Erik, *Marginal Adaptation of a Restorative Resin Polymerized at Reduced Rate*, Scand J. Dent. Res. 1991; 99: 440-4.

* cited by examiner

APPARATUS AND METHOD FOR CURING MATERIALS WITH LIGHT RADIATION

RELATED APPLICATIONS

This application is a continuation of U.S. Ser. No. 09/632,260, filed on Aug. 4, 2000, now U.S. Pat. No. 6,692,251 and entitled "Apparatus and Method for Curing Materials with Light Radiation," which, in turn, is a continuation-in-part of U.S. Ser. No. 09/009,205, now U.S. Pat. No. 6,200,134, filed on Jan. 20, 1998 and issued on Mar. 13, 2001, which application and patent are incorporated herein by reference in their entireties.

FIELD OF THE INVENTION

This application is related to the curing of materials with radiation and, more specifically, to curing dental coating and filling compounds with light.

BACKGROUND OF THE INVENTION

Curable adhesive compounds and bonding or filling compounds are widely used for structurally connecting object surfaces together or for filling gaps, openings and cavities in an object surface. Such curable compounds are generally manipulated and positioned on the object surface in a semi-solid state and are then hardened or cured in position to a more solid and permanent state. The curing or hardening of applicable compounds is generally a chemical process which is promoted and driven by one or more curing conditions or factors. For example, the curing process may be driven by exposure of the semi-solid compound and components thereof to air or by exposure of such a compound and its components to an energy source, such as a heat source.

Other curable adhesive and filling compounds are cured by exposure to radiated energy, such as visible and non-visible light energy. Such compounds, referred to as light-curable compounds, are manipulated in a semi-solid form into an area or onto a work surface. Light radiation, preferably in the form of a light beam at a specific wavelength or band of wavelengths, is then directed onto the compound. The compound includes light-sensitive chemical components therein which, when exposed to the light at the specific wavelength, promote the curing or hardening of the compound in the desired position on the work surface to bond, fill, or coat the surface.

As an example, light-curable filling and adhesive compounds are widely used in dental procedures. Dentists use light-curable dental compounds for coating and sealing tooth surfaces, filling caries and other cavities in the tooth surface, and securing crowns and various other dental structures to a tooth surface. Conventionally, dental compounds are cured by exposure to light in the blue range of the spectrum. Once cured, the dental compound reduces further tooth decay, bonds the dental structure, and/or provides additional structure to a tooth. Therefore, it is important that the compounds are completely cured.

More specifically, for curing light-curable dental compounds, visible blue light, and particularly a blue light beam from a hand-held curing light device, is directed onto a tooth surface containing the desired compound layer. The blue light penetrates into the compound layer on the tooth surface for complete curing. The duration of the exposure to blue light for proper curing of the compound layer is dictated by the type of compound and the thickness of the compound layer, as well as the power level and characteristics of the blue light from the curing light device. For example, a thin tooth surface coating or veneer will require less radiated light power, while thicker, deeper fillings for caries and other cavities will require a greater amount of radiated power directed onto the tooth surface for proper curing.

While light-curable compounds have shown very beneficial results in the dental field, existing techniques and dental curing light devices utilized to deliver the light to the tooth surface have various drawbacks. For example, existing dental curing devices require specific filtering mechanisms. Filtering must be done for several reasons. First, it is known that certain wavelengths of blue light are harmful to human tissue. While attempts are made to direct the light beam only on to the tooth surface, a certain amount of oral tissue exposure to the light is inevitable. Therefore, harmful wavelengths must be filtered. Additionally, light-curable compounds are usually sensitive to light having a somewhat specific wavelength, such as a specific blue light wavelength with currently available dental compounds. Therefore, a dental curing light filtering device is tuned to emit light at the proper wavelengths for both patient safety and proper curing.

Many existing conventional dental curing lights use broad spectrum lamp elements, such as halogen bulbs. As a result, dental curing lights must utilize special and complicated filtering devices or filters which receive the broad spectrum light from the lamp element, and then filter the light to provide only the light at the desirable wavelengths. Available lamp elements deliver a wide spectrum of radiation, including visible light, UV light, and infra-red light. Therefore, prior art curing techniques and light devices have generally been very inefficient, because a large amount of the radiated light power is lost simply due to filtering of a significant part of the light spectrum. For example, the input power to a conventional halogen bulb may typically be around 80 Watts, whereas the output power from the dental light device of light at the desired blue wavelength, for example 400–500 nanometers, is typically less than one-half (0.5) Watt.

Additionally, the efficiency of the prior art dental curing lights is further degraded by power losses due to the angle of incidence of the radiated light upon the filtering element. For example, many prior art curing lights utilize reflective filters which reflect only the light at the desirable wavelengths, such as blue light, onto the tooth surface and dental compound. Light at the undesirable wavelengths is passed through the filter to a light absorbing component where it is dissipated. If the angle of incidence of the light from the halogen bulb varies significantly from the desired angle of incidence for the filtering element surface (e.g., 45°), then a reduced amount of the desirable light is reflected onto the tooth surface. This further decreases the amount of desirable light power which is available for curing the dental compound. Conversely, a higher amount of light at undesirable wavelengths may also be reflected onto the tooth surface, rather than being transmitted through the filtering element to be dissipated.

Still another drawback with prior art curing lights is that they generate significant amounts of heat and therefore require complicated cooling systems to operate within the proper temperature range. The significant amount of light energy at the undesirable wavelengths, which is generated by the halogen bulb, must be filtered or otherwise captured. The captured or filtered energy is then dissipated in the form of heat. Therefore, power absorbing and heat dissipating elements are required within conventional curing light devices.

Thermal shields are often utilized in conjunction with reflective filters to absorb and dissipate the unreflected, unused light energy in the form of heat. The high power output required for the halogen bulb to produce the desired light power level for curing, creates a significantly high thermal load on the shields. The shields must then be cooled. Generally, fan elements are used in the dental light device to provide convective cooling to the shields. The additional cooling elements increase the size of the light device and complicate its design. As will be appreciated, it is desirable to keep the light device as small and maneuverable as possible, since it is hand-held and used in a patient's mouth.

Additionally, a thermal load is also placed on the reflective filter element, which must then also be cooled, such as by heat sinks and fans. The absorption devices and heat dissipating systems not only complicate the operation and design of the light device, but also make it more expensive to produce, and more subject to operational failure.

Another drawback of prior art dental curing light devices is the limited operational life of the lamp element, such as a halogen bulb. The bulbs frequently burn out and must be replaced. Furthermore, the heat generated inside the light device, which is usually enclosed, shortens the effective operational lifespan of the bulb.

Attempts have been made in the prior art to address some of these drawbacks. For example, Japanese Patent Applications No. 6-30275, 6-285508, 7-163863, and 8-194786; U.S. Pat. Nos. 5,420,768 and 5,634,711; and U.K. patent application No. GB 2,329,756, all disclose various devices using packaged, conventional light-emitting diodes or LEDs, to provide a curing light source with light in the desirable blue range. While specific blue light is provided by the LEDs without significant filtering, various of these devices require complicated internal designs for focusing of the curing light, or require specific electronic control of the LEDs. Furthermore, large numbers of conventional LEDs are necessary. As illustrated in the Figures of those applications, the solid state LED elements are spread out over a circuit board or other support structure and require a somewhat large housing to contain all of the conventional LEDs necessary for generating the intensity of light which is required for practical curing uses. Therefore, it has been difficult to provide a suitable curing light using conventional LEDs, which will generate sufficient curing power in a small incomplete design.

Using traditional packaged LEDs, as disclosed in the above-cited art, has specifically presented difficulties associated with generating sufficient curing power within a reasonably sized device which may be adequately cooled. Further complications with such devices have resulted from attempts to concentrate the light from the large grouping of traditional LEDs into a small area and at a sufficient power density so as to be useful for curing. Such difficulties in providing a suitable curing light device utilizing the existing traditional packaged LED technology is highlighted by the lack of a well-received and widely-utilized dental curing light on the market which utilizes such technology.

Alternatively, the devices and technology disclosed in U.S. patent application Ser. No. 09/009,205, noted above, have provided a curing device with solid state, light-emitting components which generate sufficient curing power densities in a reasonably-sized device that may be properly cooled. Further efforts by the inventors of the present application are continuing to improve the existing technology disclosed in that earlier application and to provide the desirable curing power density, size and thermal characteristics required for a successful commercial curing device.

Still another drawback associated with prior art curing lights is their inefficiency in transmitting the light to the work surface, such as a tooth surface, once the light has been generated by the element or bulb. The light is generated within the main housing of the curing light, and must be transmitted to an output end of the housing. Existing dental curing lights utilize elongated light guides to deliver light from the light generating elements inside the housing to the tooth.

Light guides are usually comprised of a large number of optical fibers fused together into an elongated guide. The air/glass interfaces between the generating elements and the input end of the light guide and the output end of the light guide and the inside of the mouth are inefficient and may produce approximately a 10% loss in power per interface. Furthermore, prior art devices may utilize a converging lens to focus light into the input end of the light guide. This provides another lossy interface encountered by the light. Such inefficiencies further increase the cure time that is necessary, and/or create the need for higher power (and associated heat) to provide the necessary curing light intensity.

Another concern with dental curing lights is that such lights are medical/dental instruments, and a portion of the instrument is introduced into a cavity of the body, i.e. the mouth. Since the same curing light will be utilized with different patients, cross-contamination between patents must be avoided. Accordingly, sterilization of the curing light, or a portion thereof, has been necessary with conventional devices. Sterilization, often referred to as autoclaving, requires additional equipment which must be purchased and maintained by the dentist or other physician. Sterilization also introduces an extra step in between curing procedures. Furthermore, the high heat required for sterilization may, over time, damage components of the curing light. Accordingly, conventional curing lights must be designed to withstand sterilization and the high temperatures associated therewith of to otherwise address the sterilization issue.

Accordingly, it is an objective of the present invention to provide a simple, durable curing light device for hardening or curing light-curable compounds. Particularly, it is an objective to provide such a curing light device for curing dental compounds used for dental fillings and coatings.

It is another objective to provide a curing light utilizing solid state light elements.

It is another objective to provide a curing light which has a compact and simple design and which is capable of providing a light power density that is useful for practical curing applications.

It is still another objective of the present invention to cure compounds with curing lights utilizing less power and having greater efficiency to reduce the amount of heat energy generated by the device and thus reduce the heat energy which must be dissipated. Furthermore, it is desirable to provide more efficient cooling of the light-generating devices.

It is still another objective of the invention to eliminate the necessity of reflective filters and other filter elements within a light device for curing light-curable compounds.

It is still another objective to address the need for sterility within a curing light.

It is still a further objective to provide a blue light device which operates within a small space and is easily manipulated within the mouth of a dental patient.

These objectives and various other objectives will become more readily apparent from the Description of the Invention below.

SUMMARY OF THE INVENTION

An instrument and method for curing light-curable compounds, such as dental compounds in the mouth of a patient, comprises a housing which supports a plurality of solid state, light-emitting elements. The elements are preferably light-emitting dies formed of a semiconductor material. The elements are mounted on a substrate supported by the housing to form a collective array which is operable for collectively emitting light having a wavelength within a narrow band of wavelengths. In one embodiment of the invention, the narrow band of wavelengths includes that of the blue wavelength. However, other wavelengths might also be utilized, depending upon the light sensitivity of the curable compound utilized.

One suitable housing for the invention includes a gun-shaped housing which has a handle portion and a barrel portion. The handle portion is held by an operator and the barrel portion is directed toward a work surface, such as a tooth. A portable power supply may be utilized within the housing such that the instrument is a hand-held instrument which is completely portable. In one embodiment of the invention, the array of light-emitting elements is positioned on the distal end of the barrel portion of the housing which is placed within the mouth of a patient so that the light is delivered directly to a work surface, such as a tooth. In an alternative embodiment, the array of elements may be positioned in the housing such that the generated light must be transmitted to the distal end, such as by an optical fiber light guide.

In accordance with one aspect of the present invention, an optical focusing device is positioned to intercept the light emitted by the array of elements. The optical focusing device is a non-imaging optical device which is operable for collimating the light from the array into a beam to be directed on to a compound for curing the compound. The non-imaging device efficiently collimates and transmits the light from the array to a work surface without inefficiencies associated with imaging lenses in the prior art. A reflective element may be positioned between the array and the optical focusing device for further efficiently directing light from the array into the optical focusing device to be collimated and delivered to a work surface.

In accordance with another aspect of the present invention, the array of dies is arranged on a substrate in a density which is operable for emitting a power density of light in the range of 200–1400 $mW/cm^2$. Such a density provides a desirable curing power to the work surface for a suitable cure. For cooling such an array and the substrate on which the elements are mounted, the present invention utilizes conductive cooling wherein a heat tube containing a heat-conductive liquid is thermally coupled to the substrate for conductively transferring heat generated by the array of elements away from the substrate. In one embodiment of the invention, the heat sink is thermally coupled to the substrate and the heat tube is then thermally coupled to the heat sink. In that way, heat is conductively transferred away from the substrate and elements. A heat exchanger is coupled to the other end of the heat tube for convectively transferring heat to the air, such as with the utilization of a fan.

In another aspect of the present invention, a disposable sleeve is utilized over a portion of the housing during the curing process. After each curing process, the disposable sleeve may be removed and discarded, thus eliminating the requirement of autoclaving the curing instrument after each use and prior to the next use. In one embodiment of the invention, the non-imaging optical device, such as a non-imaging lens, and a reflective element are coupled to an end of the disposable sleeve. When the sleeve is positioned over a portion of the housing, the reflective element and lens are aligned coaxially with the array collimating light from the array. In such an embodiment, both the non-imaging lens and reflective element are disposable and are discarded with the sleeve after each use.

The array, which comprises a plurality of dies positioned on a flat substrate, generally emits light within a range of 0–180°. When the array is located at the distal end of the housing, the non-imaging lens and reflective element are capable of capturing the light within the 180° range and effectively and efficiently collimating the light into a beam directed to the work surface. When the array is positioned further within the housing, away from the distal end of the housing, and away from the work surface, the non-imaging lens is operable for collimating light within the 180° range into a beam which does not diverge significantly from an acceptance angle of an optical fiber light guide. In that way, light is efficiently directed through the light guide and housing to the distal end of the housing whereupon it is emitted onto a work surface, such as a tooth. Preferably, the array is mounted onto the distal end of the housing for directly delivering light to the work surface. In that way, an optical fiber light guide, which has multiple lossy air/glass interfaces, may be eliminated for efficient transmission of light.

One embodiment of the invention utilizes a single non-imaging optical focusing device for the array of elements. Alternatively, the elements might range in sub-groups on the array and multiple, non-imaging optical devices may be utilized.

BRIEF DESCRIPTION OF THE DRAWINGS

The accompanying drawings, which are incorporated in and constitute a part of this specification, illustrate embodiments of the invention and, together with a general description of the invention given below, serve to explain the principles of the invention.

DETAILED DESCRIPTION OF THE INVENTION

Figures 1, 2B:
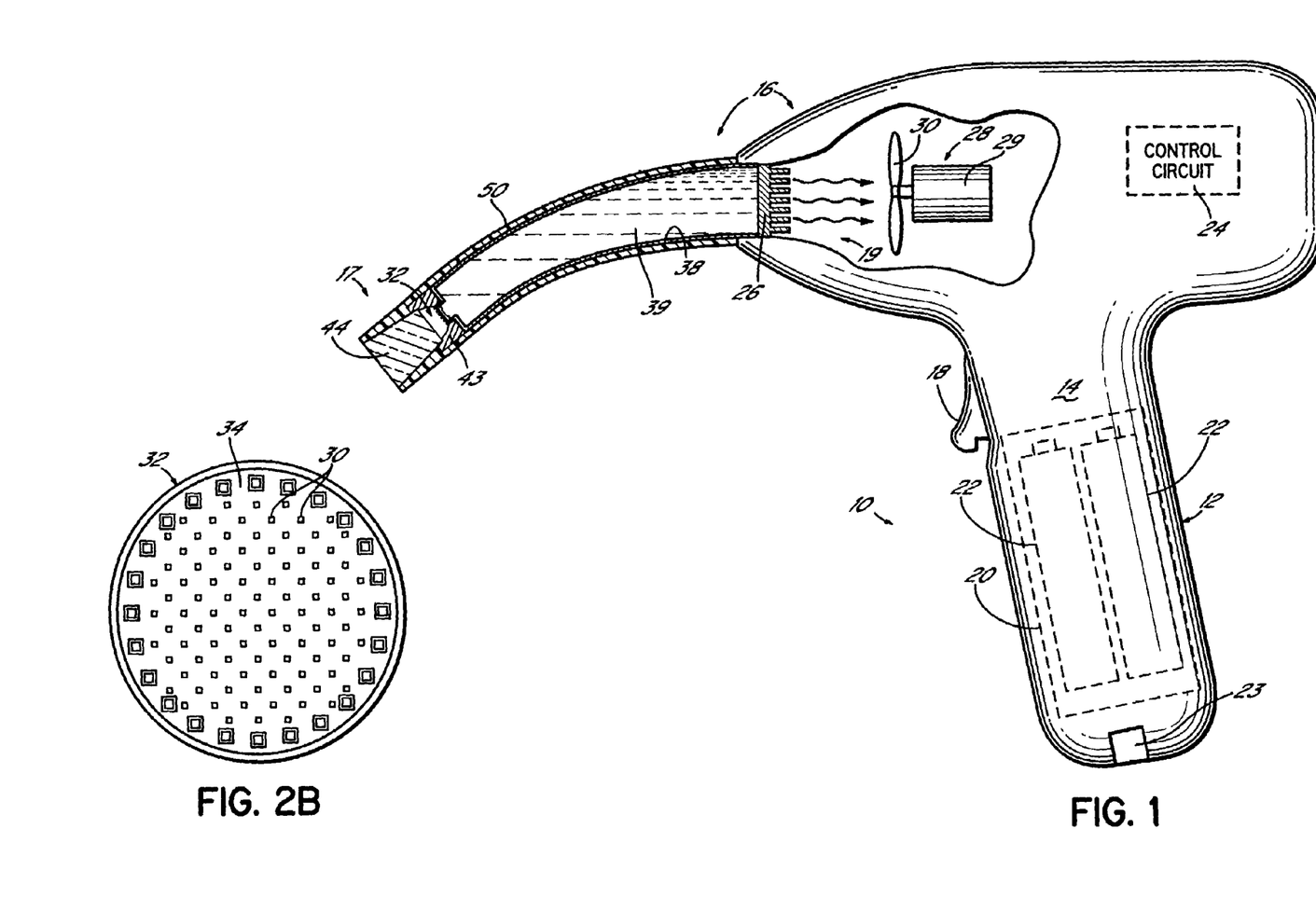
FIG. 1 is a side view in partial cross-section of one embodiment of a curing light device in accordance with the principles of the invention.
FIG. 2B is a top view of an array of dies in accordance with one embodiment of the invention.

FIG. 1 illustrates one embodiment of a curing light device or curing light for curing light-curable compounds such as dental compounds in accordance with the aspects of the present invention. In FIG. 1, device 10 includes a housing 12 which is to be manipulated for curing. Housing 12 is generally gun-shaped and includes a handle portion 14 and a barrel portion 16. The operator, such as a dentist, grips housing 12 around the handle portion 14 and directs the barrel portion 16 in the direction of the tooth surface (or other work surface) and compound to be cured (not shown). For curing dental filling and coating compounds, the dentist would generally position at least part of the barrel portion in the mouth of a patient with a radiating end 17 of the barrel portion pointing at a particular tooth or teeth. The handle portion 14 includes an operational trigger switch 18 which is operably coupled to a power supply 20 and/or control circuit 24 for selectively operating the device and supplying power to light-emitting elements 32 to generate a curing light beam, as discussed further below. The power supply 20 is shown located in handle portion 14, but might also be located elsewhere in the housing.

In one embodiment of the invention, the power supply is portable and incorporates batteries 22. The batteries could be any suitable type (e.g. lithium batteries), and may be disposable or rechargeable. To that end, housing 12 may include a port 23 for coupling an external charger (not shown) to the power supply 20 to charge rechargeable batteries 22. Alternatively, an external power supply, such as one powered by an AC outlet, may be coupled to power supply 20 to provide the power necessary to operate device 10.

A control circuit 24 is mounted within housing 12 and is operably coupled to the power supply 20, trigger switch 18 and the other components of device 10, such as array 32, for operating and controlling the components. Control circuit 24, for example, may include various electrical circuit components mounted on a circuit board and arranged in a way determined by a person of ordinary skill in the art for providing the desired power and control of device 10. For example, the control circuit 24 will usually include conventional control circuits for a curing light device, such as a timer, for timing the operational radiation cycle for the device when the trigger switch is engaged. A microprocessor may also be utilized for such control, rather than discrete components. It will be readily understood that the control circuit may be configured in various different ways to properly operate curing light 10. In one embodiment, the microprocessor control will regulate the lamp voltage to produce a constant output. In other embodiments, the microprocessor control might be utilized to ramp the power up or down in a selected fashion for proper curing.

Barrel portion 16 is appropriately formed and may include an angled distal or radiating end 17 to direct a curing light beam 21 out of the housing and onto a tooth surface or other work surface. It will be understood by a person of ordinary skill in the art that the shape of housing 12 may also vary. Barrel portion 16 is shown as solid in the Figures; however, it might also be vented for heat dissipation purposes. Furthermore, the barrel portion 16 might be separate from the rest of the housing and removably secured to the housing by any suitable method as is known in the art. For example, the barrel portion 16 might be screw-mounted to the housing 12. Still further, the power supply might be positioned in line with the barrel portion to reduce or eliminate the handle portion and thereby streamline the design, such as for a small, pocket curing light. The housing 12 is formed of a suitable light-weight plastic material such as polysulphone.

FIG. 1 illustrates one embodiment of the present invention in which a beam of radiation or light 21 utilized for curing purposes is generated by an array 32 of light-emitting elements positioned proximate the radiating end 17 of the barrel portion 16. Heat generated by the array 32 is transmitted from the radiating end 17, or distal end, back to a proximal end 19 of the barrel portion, where it is further dissipated. In the embodiment of FIG. 1, a heat tube 38 is thermally coupled to the array 32 and conductively transfers heat generated by the array to a heat exchanger 26, which is then convectively cooled. An appropriate fan 28 with motor 29 and blade 30 may be mounted within the housing 12, as shown in FIG. 1 to assist convective cooling.

Figure 2:
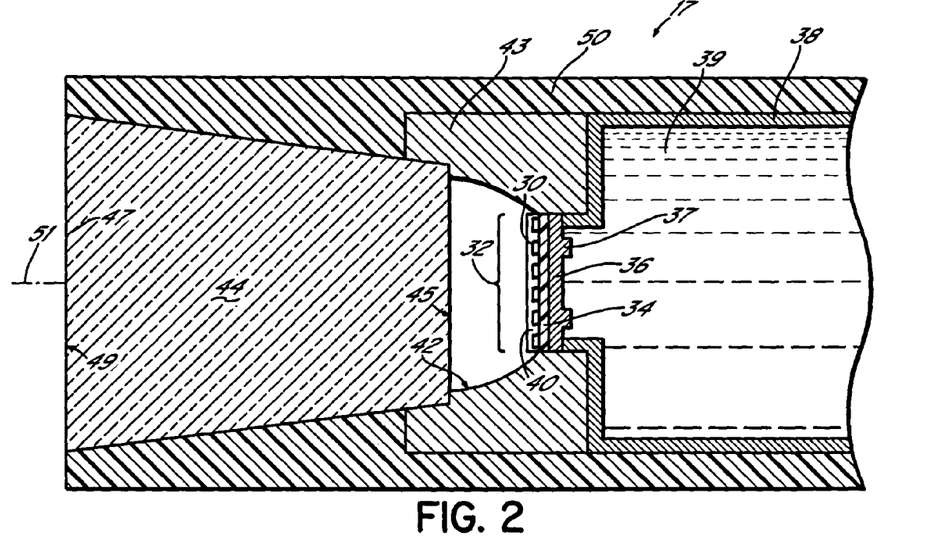
FIG. 2 is a side view, in partial cross-section, of a portion of the embodiment of the invention illustrated in FIG. 1.

More specifically, referring to FIG. 2, the illustrated embodiment of the present invention utilizes a plurality of individual light-emitting dies 30 which are mounted to form a collective array 32 on a substrate 34. The dies 30 are small, bare semiconductor junctions and are constructed using a light generating semiconductor material. The dies 30 are preferably not separately or individually packaged or otherwise mounted with individual integral lenses as are conventional light-emitting diodes or LEDs. Conventional LEDs used in the prior art have integral and individual packages, usually including a reflector and an integrally formed individual lens. The dies of the invention might be used with additional components, such as a clear protective coating 40, which is applied over the dies on substrate 34, or other added components. However, the dies as mounted are essentially bare semiconductor junctions, without prepackaged individual and integral reflectors and lenses, as are found in conventional LEDs.

As noted above, the dies 30 are not individually lensed, as are conventional LEDs. However, they might be covered with a clear protective layer or coating 40 of plastic to improve the durability of the array 32.

The substrate 34 is an electrically insulated substrate which has heat conductive properties. In one embodiment of the invention, substrate 34 may be a sapphire substrate or a diamond which has electrically insulative properties, but which also conducts heat away from the die array 32. For the purposes of uniform light generation within a beam having a generally circular cross-section, the dies of array 30 are preferably arranged in a circular pattern. U.S. patent application Ser. No. 09/009,205, illustrates several circular patterns of dies and light generating elements suitable for an embodiment of the present invention.

The substrate 34 is bonded to a heat sink 36, formed of a suitable thermally conductive material, such as copper. Heat sink 36 is then welded or soldered to one end of a liquid-filled heat tube or pipe 38 for conductively transferring heat generated by the dies 30 away from the heat sink 36, substrate 34 and array 32. A heat conductive liquid 39 contacts the back side of heat sink 36, opposite substrate 34 and array 32 (see FIG. 2), and thermally pulls heat from the sink. Therefore, the die array is effectively conductively cooled using the heat tube 38 and the intermediate elements 34, 36. Heat tube 38, which includes a heat conductive liquid 39 therein, such as saline, is commercially available from Aavid Thermal Technologies.

One particularly unique aspect of the present invention is that the array 32 is conductively cooled to provide adequate heat transfer from the light-generating dies 30. Prior art structures have traditionally relied upon convective cooling in which a heat sink and other heat dissipating devices thermally coupled to the light-generating elements are convectively air cooled, such as by a fan. One particular problem with prior art devices has been the dissipation of heat which is generated by the LEDs or other light-generating elements utilized therein. In the present invention, the heat tube 38 rapidly conductively draws heat away from array 32 and dies 30 for improved cooling characteristics. This allows a sufficient amount of curing light power to be generated for proper curing while maintaining an array which does not overheat. The present invention therefore provides improved heat transfer and dissipation capabilities with respect to the prior art.

Referring again to FIG. 1 and the embodiment of the invention which utilizes the array 32 located at the distal, or radiating end 17 of barrel portion 16, the opposite, or proximal, end of the heat tube 38 is thermally coupled to a heat exchanger 36, which is then convectively cooled by fan 28. The heat exchanger, which may be soldered to the heat tube 38, has fins, as shown, over which air is directed. Therefore, the die array 32 is conductively cooled by the heat tube 38 and a liquid therein, and the heat tube is then convectively cooled at the opposite end by air, such as by a fan.

For directing and collimating the beam 21 generated by array 32, the embodiment of the invention illustrated in FIG. 2 utilizes a reflective surface 42, and an optical focusing device 44 to collimate light from the array 32 into a beam to be directed into the mouth of the patient for curing compound therein or to be directed to some other work surface. As shown, the array 32, reflective surface 42 and optical focusing device 44 are all positioned at the distal end of the barrel portion. Thereby, the light is directly radiated onto the work surface and compound. Therefore, the embodiment of FIGS. 1 and 2 eliminates various air-to-object interfaces which tend to be lossy. As such, the present invention more efficiently delivers power from the light generating elements to the work surface. Generally, the radiating or distal end 17 will be positioned in the mouth of the patient to radiate a beam of light directly onto a work surface with a light-curable compound. Prior art devices using light transmitting devices with multiple lossy interfaces often have difficulty in generating sufficient light power densities for curing. The present invention addresses this issue by eliminating various lossy interfaces.

To focus the light from array 32, the curing light device 10 uses a reflective surface or reflector 42 which encircles the array as shown in FIG. 2. In the illustrated embodiment, the reflective surface 42 is formed by an appropriately shaped plastic ring structure 43, which circumferentially surrounds the outer edge of array 32 defined by substrate 34. Reflective surface 42 is generally parabolic in shape and is formed by coating the surface 42 of plastic structure 43 with a reflective coating for the purpose of efficient reflection. A mylar coating, available from 3M, has proven to have suitable properties for that purpose and has an approximately 99% reflective efficiency for the purposes of the present embodiment of the invention illustrated in FIG. 2. As shown in FIG. 2, the plastic ring structure 43 forms the generally parabolic reflective surface 42 around array 32 for directing the light away from the dies 30 and into an input end 45 of the optical focusing device 44.

The optical focusing device, in accordance with one embodiment of the invention, is a non-imaging device. One suitable non-imaging optical focusing device is a non-imaging lens 44 having a generally truncated conical shape, as illustrated in FIG. 2. A non-imaging lens, such as lens 44, receives the light from array 32 at an input end 45 and directs and concentrates the light from array 32 into a focused beam at the output end 47 of the non-imaging lens 44. However, the non-imaging lens does not form an optical image, which is inefficient. A non-imaging optical focusing device as used in the present invention efficiently collimates light so that a desirable light power density is achieved at the work surface, such as a surface of a tooth. The light power density from the array 32 is not reduced by the formation of an image as with traditional optical lenses. One suitable, non-imaging lens is formed of a transparent polycarbonate material. As illustrated, structure 43 is appropriately formed to receive the input end 45 of lens 44 to position the lens in coaxial alignment with the array 32 and surface 42 about axis 51. Each of the lens and surface 42 preferably have generally circular transverse cross sections for efficient transfer of the light along axis 51. One suitable combination of a reflective surface and optical focusing device, which are operably coupled together, is available from Teledyne, of Hawthorne, Calif.

Figure 2A:
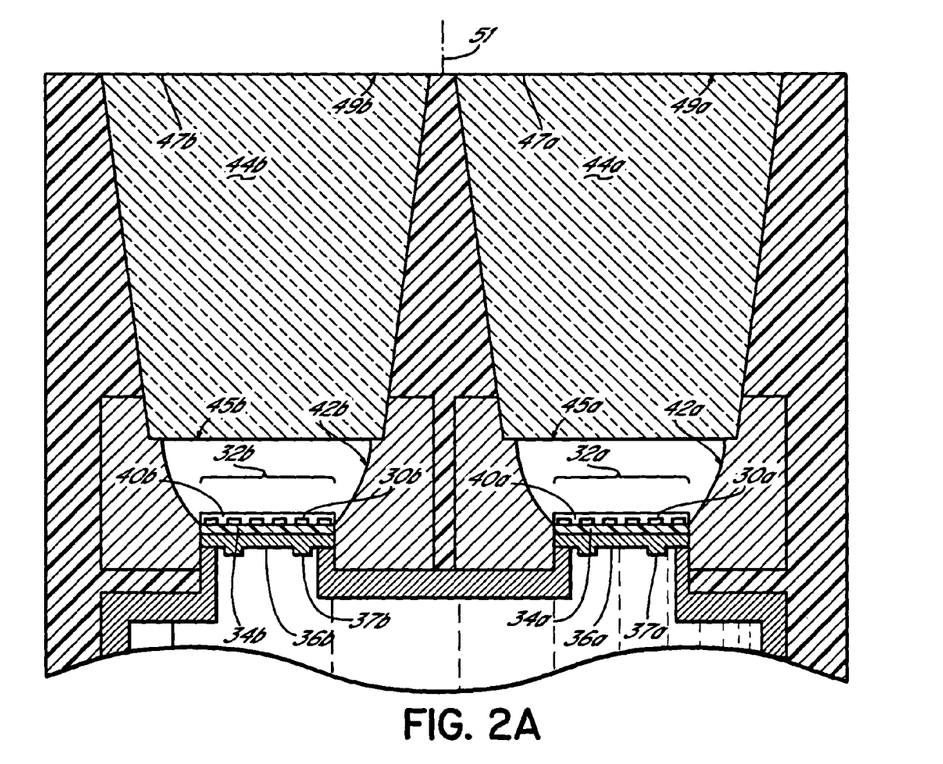
FIG. 2A is a side view, in partial cross-section, of a portion of another embodiment of the invention.

The embodiment of the invention illustrated in FIG. 2 shows a single non-imaging optical focusing device 44 for the array 32 of dies. In accordance with another aspect of the present invention, it is anticipated that multiple non-imaging optical focusing devices might be utilized. For example, referring to FIG. 2A, substrate 34a may include multiple groups of dies, 30a, 30b, which are arranged on the substrate 34a to operate as separate groups of light-generating elements. To that end, a non-imaging optical focusing device 44a may be associated with one group of dies 34a, while another non-imaging optical focusing device 44b may be associated with dies 30b of the other group. Of course, greater numbers of non-imaging optical focusing devices may be utilized for other discrete groups of dies. Generally, however, there will be a substantially smaller number of non-imaging optical focusing devices than there are individual dies. That is, in the embodiments of the invention illustrated in FIGS. 2 and 2A, a single non-imaging optical focusing device will serve a multiple number of individual light-emitting dies. The multiple focusing devices will cooperate to transmit light along axis 51.

In accordance with another aspect of the present invention, the barrel portion 16 of the device 10, particularly the distal or radiating end 17 of the barrel portion, is inserted into the mouth of the patient for curing compound therein. Accordingly, before use with the next patient, it will be appreciated that the device would have to be sterilized. Prior art devices must be sterilized, such as by autoclaving, as mentioned above, which further complicates and delays the curing procedure. The present invention provides a unique construction which eliminates the requirement of a sterilization process and thereby makes the curing process simpler, quicker, and more cost-effective.

To that end, the invention utilizes a removable sleeve which may be separately autoclaved. Alternatively, as mentioned, the sleeve may be disposable to be discarded after one use. Specifically, in the embodiment of the invention illustrated in FIGS. 1 and 2, the ring structure 43 forming reflective surface 42 and the adjacent non-imaging lens 44 are mounted and secured within a disposable sleeve 50. The sleeve 50 is made of a suitable disposable plastic, such as PVC, and the sleeve is configured for being positioned over at least a section of the barrel portion 16 of the device 10. Preferably, the sleeve is configured to extend over a significant section of the barrel portion 16, and at least over the part of the barrel portion 16 exposed to the mouth of a patient. In the embodiment illustrated in FIG. 2, the PVC sleeve 50 is configured to be positioned over the heat tube 38 and array 32. The sleeve 50 is configured to position the lens 44 and reflective surface coaxially with the array 32. In one embodiment of the invention, once the device has been used for curing, the PVC sleeve 50, ring structure 43, and non-imaging lens 44, may then be removed from the heat tube and away from the array 32 of light-emitting dies. The sleeve, including the lens and reflective structure 43 are then discarded with the sleeve 50. Alternatively, the sleeve and lens and reflective structure could be removed and autoclaved and then placed back in position.

In an alternative embodiment, only the sleeve might be disposable. The lens 44 and ring structure would then remain with the array 32 or could be separately positioned with the array apart from sleeve 50. In such a case, only the sleeve would be discarded or autoclaved.

The device and the component parts, including the heat tube 38, heat sink 36, substrate 34, and dies 32, are not been directly exposed to a patient because they are covered by the sleeve. In the embodiment where the lens and structure 43 are separate from the sleeve, those parts will be isolated as well. Therefore, the isolated or covered components do not have to be sterilized or autoclaved as required with prior art devices and methods. Thereafter, a new sleeve, possibly including a new reflective structure 43 and lens 44, is inserted onto the heat tube 38 and barrel portion 16 and aligned with the array of dies 32 for the next use. The present invention therefore reduces the possibility of contamination between dental patients and further enhances the curing method by eliminating the sterilization process. As a result, the curing process is simpler and more efficient because a sterilization step is not necessary between patients. The process is also more cost effective as autoclaving equipment does not have to be purchased and operated to sterilize the curing light.

The present invention as illustrated in FIG. 2 also improves upon the prior art by delivering a beam of light from a source close to the work surface (e.g., a tooth). Specifically, the distal or radiating end 17 of the barrel portion 16 is positioned at or proximate a tooth surface containing the curable compound. With the light delivered directly from the array 32 to the surface through only the non-imaging lens 44, numerous lossy air/glass interfaces are eliminated between the die array 32 and the output surface 49 of the device 10. Conventionally, the light generating elements have been positioned away from the work surface and inside the housing such that a fiber optic light guide was necessary to transmit the light to the work surface. Furthermore, with such light guides, it is often necessary to use a converging optical lens before the light guide so that the generated light may be efficiently focused into the input end of the light guide. Light guides and converging lenses present lossy air/glass interfaces to the light beam. It has been estimated that air/glass interfaces may produce light power losses in the range of approximately 10% per interface. By eliminating the interfaces between the dies 30 and the tooth surface, the present invention light transmits light in an efficient, collimated form with less of the power loss at the various interfaces that are required in the prior art. Therefore, the present invention provides efficient transmission of a collimated light beam to the work surface of the tooth and curable compound thereon. With more efficient transfer of light, a smaller number of dies 30 in the array 32 may be used while still providing a sufficient light intensity or light power density at the output surface 49 of the lens. In that way, the invention may provide suitable curing power levels in a generally compact and easily manipulated device. Furthermore, with less loss at the interface, less heat is generated, further improving on the prior art.

In the preferred embodiment of the invention, the dies 30 are positioned in the array 32 with a density sufficient to provide a light power output density at the desired wavelength in the range of approximately 200–1400 mW/cm$^2$. In one embodiment of the invention, the dies are generally square in shape, and are 0.010 inches per side. The dies are spot welded to the substrate and specifically to leads (not shown), which are electrically coupled to a control circuit 24 and/or power supply 20. The die substrate is preferably is circular, having a diameter of approximately 0.19 inches (approximately 4.8 millimeters).

A suitable number of dies are positioned on substrate 34 to generate the desired light and power density at the output surface 49 of the non-imaging optical focusing device 44. Generally, in one embodiment of the invention, 30–60 dies are suitable for generating desirable curing light power densities. Of course, a greater or lesser number of dies may be utilized in other embodiments of the invention.

Because of the unique cooling arrangement of the present invention utilizing conductive cooling, the reduction of lossy interfaces and the overall configuration of the embodiment of the invention disclosed herein, the dies may be driven at a sufficient power level to yield the desired light power output or light density, in the range of approximately 200–1400 mW/cm$^2$. Generally, the dies may be driven by 12 volts DC in series sets of 3 dies.

For example, one embodiment could be a 34 die lamp which may be operated at 8.13 Watts (8.7 V and 0.935 A). Such a design proved efficient and performed a suitable job of curing. Another embodiment might use 60 die or a higher power output (e.g., a 67% increase in power).

In one embodiment of the invention, series groups of three dies are connected in series to a 12 Volt DC source through a current-limiting resistor. To that end, each die is then driven with approximately 4 volts DC. Furthermore, by utilizing a 12 Volt source, the fan may also be driven by that DC source. It may be readily understood that other arrangements of dies may be utilized, driven by sources having various different power or voltage output levels.

Preferably, the dies 30 are positioned in the array 32 in a sufficient density to provide a curing light which has a suitable light power output for proper curing, but which does not overheat tissues surrounding the work surface, such as a tooth. The inventive lamp will provide less heat to the tissue than a halogen lamp. For example, an embodiment with 34 die as described above yielded a radiometer reading of 200 mW/cm$^2$, while a comparable cure with a 52 Watt halogen lamp yielded readings around 600 mW/cm$^2$. Because of the much lower radiometer readings, tissue damage should not be as significant an issue with the invention as with a halogen light.

With current dental applications, it is desirable to utilize a die array 32 which generates blue light in a wavelength range of approximately 130 nanometers to 470 nanometers because current compounds are sensitive to blue light. While such blue light is suitable for current dental applications, the present invention is not limited to only blue light wavelengths for curing purposes. Rather, the present invention may be utilized with compounds that may cure utilizing light at other various wavelengths.

Furthermore, the non-imaging optical focusing device 44 may be sized appropriately depending upon the application. For example, a lens having an 8 millimeter cross-sectional diameter at the output surface 49 may be utilized for small curing applications, whereas a lens having a cross-sectional diameter of 11 millimeters at surface 49 might be utilized for larger curing applications. As may be appreciated, to ensure efficient transfer of curing light to the work surface, it is desirable that a majority, if not all, of the light generated by the dies of array 32 is transmitted into and out of the non-imaging optical focusing device 44. To that end, the reflective surface 32 is shaped and configured in diameter to ensure that the light beam is collected and reflected into the input end 45 of the optical focusing device 44. In the illustrated embodiment, the output end 51 of the reflective surface which interfaces with the input end 45 of the optical focusing device is smaller in diameter than the input end 45. In that way, the light reflected by surface 42 is captured by the optical focusing device 44. The non-imaging optical focusing device 44 is not restricted by a focal length, since it is a non-imaging device. In that way, the device 44 captures and collimates the light beam for efficient transmission to a work surface, such as a tooth. Therefore, the present invention is not particularly sensitive to the distance which the output end 49 is maintained from the tooth surface. Of course, it is generally desirable to position the output end 49 as close to the tooth surface as possible for efficient curing.

In accordance with another aspect of the invention, the dies 30 might be evenly arranged on substrate 34 to form a generally circular array, as illustrated in several of the embodiments disclosed in U.S. patent application Ser. No. 09/009,205, and as illustrated in FIG. 2B. The dies might also be mounted in various groupings, such as subgroups of four or some other number, and then such subgroups would be mounted on the substrate. That is, sub groups of multiple dies could be individually mounted and electrically coupled together, and subsequently the subgroups could be mounted on the substrate with other subgroups. As such, the invention would not be limited to individual mounting of all of the dies.

Figures 3, 4:
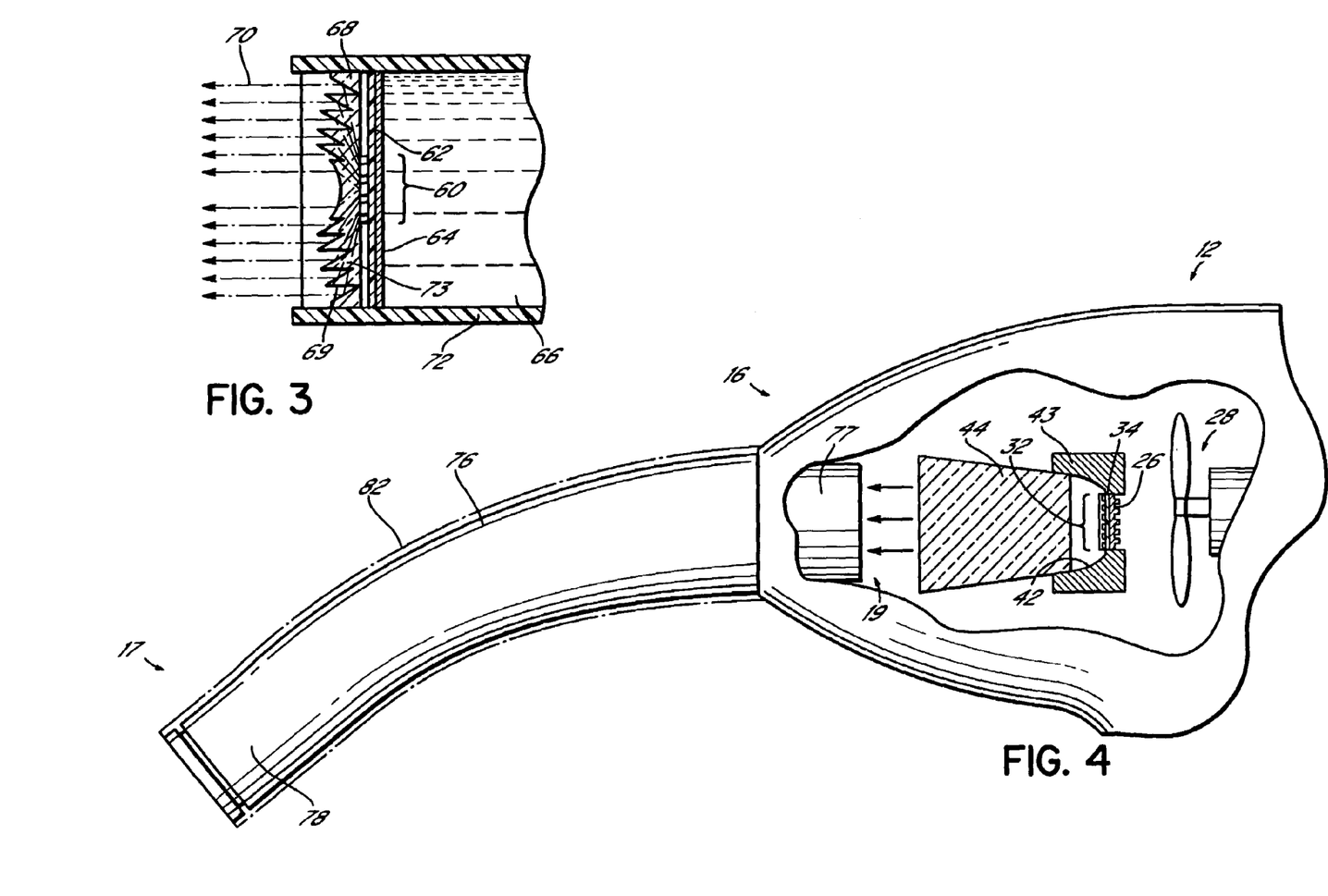
FIG. 3 is a side view, in partial cross-section, of a portion of another embodiment of the invention.
FIG. 4 is a side view, in partial cross-section, of a portion of another embodiment of the present invention.

FIG. 3 illustrates another embodiment of the invention wherein the die array is also positioned proximate the distal, or radiating end 17 of the barrel portion 16 of the housing. In the alternative embodiment, the structure is somewhat similar to the device 10 illustrated within FIGS. 1, 2, and 2A, with a different construction at the distal or radial end 17, as illustrated in FIG. 3. Specifically, the alternative embodiment utilizes an array of dies 60 mounted on a substrate layer 62. The substrate layer could be sapphire or diamond which has suitable thermally conductive properties for heat dissipation while remaining electrically insulated. Substrate 62 is then bonded to a heat sink 64 which may be made of a suitable material, such as copper. The die array 60 and the assembly including the substrate 62 and heat sink 64 are then welded or soldered onto an end of a liquid-filled heat tube 66, which conductively transfers heat away from the heat sink. In that way, the alternative embodiment of the invention utilizes the advantages provided by the above-discussed embodiment, due to the conductive cooling of the substrate and die array. As illustrated in FIG. 1, the opposite end of the heat tube 66 is coupled to the heat exchanger 26 which is convectively cooled, such as by a fan 28.

To focus light from the die array 60 in an efficient manner into a collimated and focused light beam, the embodiment of the invention shown in FIG. 3 utilizes a total internal reflection, or TIR lens. TIR lenses are known (e.g., U.S. Pat. No. 4,337,759) and are commercially available, such as from TIR Technologies, a division of Teledyne. TIR lenses are more efficient than typical Fresnel lenses, and provide a collimated beam of light generated by the die array 60. The TIR lens structure 68, shown in FIG. 3, utilizes a series of saw-tooth surfaces 69 for collimating light from the array 60 at various different angles into a beam of light 70 focused in a direction generally perpendicular to the plane of the array, as illustrated by reference numeral 70. In that way, light from the array may be efficiently delivered to a curable compound on a work surface. Preferably, the TIR lens is a non-imaging optical focusing device. The lens 68 is appropriately arranged to be generally coaxially aligned with array 60 for efficient light transmission.

In accordance with one aspect of the present invention, the TIR lens 68 is formed of a suitable polycarbonate. As discussed above, lens 68 may be incorporated with a disposable sleeve 72 positioned around the heat pipe 66. When an application is complete, the sleeve 72 and TIR lens 69 may be removed and discarded, thus eliminating the need to further sterilize or autoclave the device 10. Alternatively, lens 68 may be separately positioned with respect to sleeve 72 to be separately discarded or to remain with the array 60. The embodiment illustrated in FIG. 3 further provides efficient delivery of light from the die array to a work surface because the die and lens are positioned at the radiating or distal end 17 of the barrel portion to be directly adjacent to the work surface. In that way, various air/glass interfaces are eliminated to reduce power losses associated with such interfaces, as discussed above.

The array 60 of LEDs might be arranged and dimensioned similarly as discussed above with respect to the embodiment illustrated in FIG. 2. The TIR lens 68 will generally have a circular cross-sectional diameter significantly greater than the circular cross-sectional diameter of the array in order for the lens to capture light which is generated by the array at very small angles with respect to the plane of the array 60. In the embodiment illustrated in FIG. 3, a reflector is not utilized between the die array 60 and the lens 68. Therefore, the lens must be sized appropriately to capture low angle light, such as that illustrated by reference line 73.

FIG. 4 illustrates an alternative embodiment of the invention in which the die array is positioned more centrally within the housing and spaced rearwardly from the barrel portion. Specifically, a die assembly, similar to that illustrated in FIG. 2, is mounted in the housing proximate the proximal end 19 of the barrel portion. The substrate 34 is then coupled directly to the heat exchanger 26, which may be convectively cooled, such as by a fan 28. The barrel portion 16, rather than housing a heat tube, houses a light pipe or light guide 76. Such light guides are commercially available and come in a variety of different sizes. Generally, such light pipes are formed of a plurality of optical fibers (for example, approximately 5,000 fibers which are fused into a single light pipe structure). The beam of light transmitted into the input end 77 located at the proximal end 19 of the barrel portion 16, is transmitted through the light pipe and is directed out the transmission end 78 of the pipe at the distal end 17 of the barrel portion 16. The light pipe may maintain uniform diameter from the input end 77 to the output or transmission end 78, or may taper from one diameter to a smaller diameter at the transmission end 78. Preferably, the light pipe is bent to follow the bent barrel portion 16, illustrated in FIG. 4, so that the beam of light is directed downwardly, such as into the mouth of the patient. Alternatively, the light pipe itself may form part of the barrel portion and may be attached to the housing 12, such as by being screwed into the housing.

The non-imaging optical focusing device, such as a non-imaging optical lens 44, is used to focus the light into the light pipe. The input end 77 of the light pipe is dimensioned appropriately so that light is efficiently delivered through the focusing device 44 to the light pipe 76. To that end, the focusing device 44 collimates the light so that it does not diverge beyond the input end 77 of the light pipe.

Generally, light pipes have a defined angle of acceptance at their input end 77, such as 40°. Light directed outside of that acceptance angle is not captured by the light pipe and transferred to the work surface. The reflective surface 42 and non-imaging optical focusing device 44 utilized in the embodiment in FIG. 4 are designed to generate a beam of light which does not diverge more the acceptance angle of the light pipe. In that way, energy is efficiently translated from the array which outputs light in generally a 180° angle. Therefore, the present invention utilizes a non-imaging optical focusing device which collimates light from a 180° light output source to a column which does not diverge more than the acceptance angle of the light pipe to which the light is input.

In still a further embodiment of the invention, the die array and the TIR lens structure similar to that shown in FIG. 3 might be utilized within the housing as shown in FIG. 4. To that end, the die array 60, substrate 62, and heat sink 64 are coupled to the appropriate heat exchanger, which is then convectively cooled, such as by a fan. In such an embodiment, as well as in the embodiment illustrated in FIG. 4, device 10 would generally have to be sterilized or autoclaved after each use. However, since the die array and optical focusing devices are positioned inside the handle portion of the housing, they would be protected from the high temperatures associated with such sterilization.

Alternatively, as illustrated in FIG. 4, a disposable sleeve 82 might be utilized with the embodiment to cover the light pipe. The disposable sleeve 82 may be discarded with each use, thus effectively eliminating the required autoclaving step.

While the present invention has been illustrated by the description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details representative apparatus and method, and illustrative examples shown and described. Accordingly, departures may be made from such details without departure from the spirit or scope of applicant's general inventive concept.

The invention claimed is:

1. An instrument for curing light-curable compounds which are curable in the mouth of a patient, the instrument comprising:
   a housing;
   a plurality of solid state, light-emitting elements, the elements comprising semiconductor junctions and being mounted on a substrate supported by the housing to form a collective array on said substrate, the array of elements operable for collectively emitting light having wavelengths within a narrow band of wavelengths;
   a generally clear layer simultaneously covering all of the plurality of light-emitting elements for protecting the array of semiconductor junctions;
   an optically reflective element coupled to surround the plurality of light-emitting elements to capture the collective light from the array of light-emitting elements and direct it forwardly away from the collective array and ultimately to a compound for curing.

2. The instrument of claim 1 wherein said solid state elements are light emitting dies formed of a semiconductor material.

3. The instrument of claim 1 further comprising a heat sink thermally coupled to the substrate for absorbing heat generated by the array of elements.

4. The instrument of claim 1 further comprising a thermally conductive element which is thermally coupled to the substrate for conductively transferring heat generated by the array of elements away from the substrate.

5. The instrument of claim 1 further comprising a heat exchanger which is thermally coupled to the substrate for dissipating heat generated by the array of elements.

6. The instrument of claim 1 further comprising a first heat sink element thermally coupled to the substrate for absorbing heat generated by the array of elements, and a heat exchange element thermally coupled to the heat sink for conductively transferring heat generated by the array of elements.

7. The instrument of claim 1 wherein said housing comprises a barrel portion having a proximal end spaced from a distal end of the barrel portion, the distal end being configured to be placed in the mouth of a patient, the array of light-emitting elements being positioned proximate to said proximal end, a light transmitting device being operably coupled to said array for transmitting the light beam from the array to the housing distal end.

8. The instrument of claim 7 wherein said light transmitting device comprises a plurality of fiber optic elements operably coupled together for directing said beam.

9. The instrument of claim 7 wherein said light transmitting device has an acceptance angle, said optical focusing device operable for generating a beam of light which does not diverge significantly from said acceptance angle.

10. The instrument of claim 9 wherein said array of light-emitting elements emits light in the range of 0°–180° and said optical focusing device is operable for collimating the light into a beam which does not diverge significantly from said acceptance angle.

11. The instrument of claim 1 further comprising a portable power supply positioned within said housing for portable operation of the instrument.

12. The instrument of claim 1 wherein said array of elements has a density of elements on the substrate operable for collectively emitting a power density of light in the range of 200 to 1400 mW/cm$^2$.

13. An instrument for curing light-curable dental compounds, the instrument comprising:
   a light-emitting element having a plurality of generally bare semiconductor junctions positioned together to form multiple light emitting surfaces on a substrate and operable for collectively emitting light having wavelengths within a narrow band of wavelengths suitable for curing dental compounds;
   a generally clear protective layer simultaneously covering the plurality of semiconductor junctions for protecting the junctions, the light generated by the light-emitting element passing through the protective layer;
   an optically reflective element coupled to surround the light-emitting element and protective layer and operable to capture the light generated by the light-emitting element and direct it generally forwardly.

14. The instrument of claim 13 further comprising a light transmitting device being operably coupled to the light-emitting element for transmitting the light emitted by the element toward a curing site.

15. The instrument of claim 13 further comprising a plurality of heat dissipating elements mounted behind the substrate holding the semiconductor junction for conductively transferring heat generated by the junction.

16. An instrument for curing light-curable dental compounds, the instrument comprising
   a first plurality of light-emitting elements, the first elements comprising generally bare semiconductor junctions forming a collective array operable for collectively emitting light having within a narrow band of wavelengths suitable for curing a dental compound;
   a second plurality of light-emitting elements, the second elements comprising generally bare semiconductor junctions forming a collective array operable for collectively emitting light within a narrow band of wavelengths suitable for curing a dental compound and operating separately from the first plurality of light-emitting elements;

a generally clear protective layer covering the semiconductor junctions of at least one of the pluralities of light-emitting elements for protecting the junctions, light generated by the plurality of light-emitting elements passing through the protective layer;

an optically reflective element coupled to surround at least one of the pluralities of light-emitting elements and operable to capture the light generated by the plurality of light-emitting elements and direct it generally forwardly.

17. The instrument of claim 16 further comprising a generally clear protective layer covering the semiconductor junctions of both pluralities of light-emitting elements for protecting the junctions, light generated by the plurality of light-emitting elements passing through the protective layer.

18. The instrument of claim 16 further comprising an optically reflective element coupled to surround both pluralities of light-emitting elements and operable to capture the light generated by the pluralities of light-emitting elements and direct it generally forwardly.

* * * * *